United States Patent [19]
Petcavich

[11] Patent Number: 5,912,181
[45] Date of Patent: Jun. 15, 1999

[54] METHOD FOR MOLECULE DETECTION UTILIZING DIGITAL MICROMIRROR TECHNOLOGY

[76] Inventor: Robert J. Petcavich, 4136 Palisades Rd., San Diego, Calif. 92116

[21] Appl. No.: 08/996,845

[22] Filed: Dec. 23, 1997

[51] Int. Cl.⁶ .................................................... G01N 21/64

[52] U.S. Cl. .......................... 436/151; 436/524; 436/164; 436/172

[58] Field of Search ...................................... 436/164, 524, 436/525, 527, 151, 172

[56] References Cited

U.S. PATENT DOCUMENTS

| | | | |
|---|---|---|---|
| 5,323,002 | 6/1994 | Sampsell et al. | 250/252.1 |
| 5,653,939 | 8/1997 | Hollis et al. | 422/50 |

OTHER PUBLICATIONS

L.J. Hornbeck, "Digital Light Processing and MEMS; An Overview", Texas Instruments, Inc., Dallas, Texas, undated.

L.A., Yoder, "The State of the Art in Projection Display: An Introduction to the Digital Light Processing (DLP™) Technology", Texas Instruments, Inc., Dallas, Texas, undated.

"DLP: Simple Principle. State–of–the–Art Technology", Texas Instruments, Inc., Dallas, Texas, undated.

L.J. Hornbeck, "1.0 Introduction; 2.0 DMD Architecture", including Figures 1–4, Texas Instruments, Inc., Dallas, Texas, 1997.

*Primary Examiner*—Jeffrey Snay
*Attorney, Agent, or Firm*—Juettner Pyle Piontek & Underwood

[57] ABSTRACT

Biologic molecules and pathogens in a sample substance are detected by utilizing the multiplicity of mirrors in a digital micromirror device as test sites to which molecular probes are attached and to which the sample substance is applied. A molecule or pathogen bonded on the surface of a micromirror activated with an appropriate molecular probe can be detected by optical projection or software interrogation of the array of micromirrors.

10 Claims, No Drawings

METHOD FOR MOLECULE DETECTION UTILIZING DIGITAL MICROMIRROR TECHNOLOGY

FIELD OF THE INVENTION

This invention relates to a method of detecting and screening organic molecules and biologic pathogens by employing molecular probe activated digital micromirror technology.

BACKGROUND OF THE INVENTION

A first field of science relevant to the invention is the detection and identification of biologic molecules and pathogens.

As taught, for example, in U.S. Pat. No. 5,653,939, issued Aug. 5, 1997 to Hollis et al, a multiplicity of detection sites are formed on a suitable substrate and a sample substance containing molecular structures sought to be detected and identified is applied over the sites. Each test site contains probes designed to bond with a predetermined target molecular structure. The probes in each site differ in a predetermined known manner from the probes in the other sites so that different target molecules in the sample may bond with different probes. A signal is applied to the test sites and certain electrical, mechanical and/or optical properties of the sites are detected to determine which probes have bonded to an associated target molecular structure. The bonded molecules may then be removed from the respective sites and subjected to testing and analysis.

Numerous techniques have been employed for the detection and identification of DNA, RNA, and other biologic molecules and pathogens. These techniques include autoradiography, fluorescent microscopy, charge coupled devices, electronic and optical hybridization, electromagnetic devices, dynamic random access memory devices, mechanical resonators, and the like. Each technique has its advantages and disadvantages.

A second field of technology relevant to the invention is that relating to digital light processing display technology based on a microelectromechanical systems device known as the digital micromirror device.

A digital micromirror device is comprised of thousands, even hundreds of thousands, of individual mirrors, each usually sixteen microns square, and each fabricated on hinges on top of a static random access memory (SRAM). Each mirror is capable of receiving its own unique instructions and can receive a new instruction every 1/1000th of a second.

Each micromirror is a light switch that can reflect light in one of two directions depending upon the state of the underlying memory cell. With the memory cell in the (1) state, the respective mirror rotates to a +10°. With the memory cell in the (0) state, the respective mirror rotates to a −10°. Each mirror is capable of oscillating between these positions at rates of 1,000 cycles per second to produce pulses or bursts of reflected light.

The digital light processing system is utilized in television and similar technologies to convert digital video signals into a visible digital display by transmitting to the human eye rapid digital light pulses that the eye interprets as a color analog image. The digital micromirror device, which is available from Texas Instruments Incorporated, Dallas, Tex., is a high speed reflective digital light switch which when combined with image processing, memory, light source and optics forms a digital system capable of projecting large high contrast color images with excellent fidelity and consistency.

The technology of digital light processing has not been related to the science of detecting and identifying biological molecules and pathogens.

SUMMARY OF THE INVENTION

The object of the present invention is to unite the scientific technologies above described; specifically, to utilize the digital micromirror technology of Texas Instruments for the detection and identification of biologic molecules and pathogens.

It is not the intent of the invention to belabor any of the molecule detection techniques previously employed, but instead to bring a novel and unique approach to the art of molecule detection and identification.

The objects and advantages of the invention will become apparent from the following detailed description.

DRAWINGS

Inasmuch as the digital micromirror device is well known, and the present invention is directed not to a change in the device but to a new and novel application and use of the device, drawings are not believed necessary to a full understanding by persons skilled in the art of the following detailed description and the invention therein described.

DETAILED DESCRIPTION OF PREFERRED EMBODIMENTS

The following is a detailed description of certain embodiments of the invention presently deemed by the inventor to be the best mode of carrying out his invention.

In accordance with the present invention, an array of microelectromechanical micromirrors is employed to detect, either by optical projection or through software interrogation, the presence of a molecule or biologic pathogen bonded on the surface of a micromirror that has been activated with an appropriate molecular probe. The multiplicity of mirrors in the array serve as test sites in a manner similar to the practice of the art as above described. Such use of an array of micromirrors as test sites provides a straight forward method to screen large numbers of target molecules or pathogens quickly and efficiently for bioactivity, identification, and subsequent testing.

Molecular probes can be attached to the digital mirror surfaces by physical or chemical mechanisms. A physical method comprises adsorption or absorption of the probes onto the surfaces. A chemical method comprises bonding the probes onto the mirror surfaces by either ionic or covalent bonding. By employing one or more of these methods, a wide variety of molecular probes can be attached to the mirror surfaces.

To identify new drug candidates by optical projection using this invention, a practitioner would attach different bioluminescent or chemiluminescent probes to different mirror surfaces of the array, expose the array to a sample substance containing target molecules of interest, direct an appropriate light source onto the array, and project the resulting image on a screen or other surface. Locations where target molecules react with a probe will fluoresce in the projected image and the individual test sites (micromirrors) can be addressed with software to identify the precise location and the precise probe at that location for the molecule of interest.

A software interrogation method for identifying target molecules utilizes the surface mass change on micromirrors oscillating at 1,000 cycles per second to detect the presence of molecular reactions at specific locations. For example, molecular probes can be attached to the micromirrors, the array of mirrors can then be oscillated and exposed to a sample substance containing target molecules of interest, and if there is a chemical reaction at one or more probes, the mass of the respective mirrors will change and that will cause the rate of oscillation to change, i.e., slow down. The software will detect and identify the mirror or mirrors with slower oscillation and, knowing what probe was at that location, a target candidate can be identified.

Once target molecules are located, the identified mirror location can be covered with a photomask to protect the target molecule while the rest of the mirror array is washed with an appropriate solvent. The mask can then be removed by standard photolithography techniques, the target molecule washed off the mirror, identified and tested appropriately.

The invention lends itself to high volume, fast, lost cost screening and identification of biologically active molecules and pathogens.

The objects and advantages of the invention have thus been shown to be attained in a convenient, practical, facile and economical manner.

While preferred embodiments of the invention have been herein described, it is to be appreciated that various changes, rearrangements and modifications may be made therein without departing from the scope of the invention as defined by the appended claims.

What is claimed is:

1. A method of screening sample substances containing molecular structures sought to be detected comprising the steps of
    attaching molecular probes to the surfaces of the mirrors in an array of microelectromechanical mirrors in a digital micromirror device,
    exposing the array of mirrors and attached probes to a sample substance potentially containing molecular structures responsive to respective ones of the probes for attachment of respective molecular structures to respective ones of the probes,
    activating the array of mirrors optically by exposure to light or mechanically by oscillation,
    determining whether any of the mirrors after exposure of the array of mirrors to the sample substance have an optical or mechanical action that is different from the optical or mechanical action of other mirrors for thereby determining whether any molecular structures have become attached to any of the probes, and
    identifying the mirror or mirrors, if any, having such different optical or mechanical action.

2. A method as set forth in claim 1, comprising the further steps of isolating the mirror or mirrors having such different reaction, removing therefrom the respective probe and any associated substance, and testing the same for the presence and identification of molecular structures sought to be detected.

3. A method as set forth in claim 1 including the steps of covering each identified mirror with a photomask, washing the rest of the array of mirrors, removing the photomask from each identified mirror, and testing and identifying the substance upon each identified mirror.

4. A method as set forth in claim 1 including the steps of attaching bioluminescent or chemiluminescent probes to the array of mirrors and, after exposure of the array of mirrors to the sample substance, directing a light source onto the array of mirrors, projecting the resulting image onto a surface, determining the locations within the image that fluoresce, and identifying the mirror or mirrors that correspond to the fluorescent locations.

5. A method as set forth in claim 1 including the steps of oscillating the mirrors in the array, exposing the oscillating mirrors to the sample substance, and detecting and identifying any mirror or mirrors whose rate of oscillation changes.

6. A method of screening sample substances containing molecular structures sought to be detected comprising the steps of
    attaching molecular probes to the surfaces of the mirrors in an array of microelectromechanical mirrors in a digital micromirror device,
    activating the array of mirrors optically by exposure to light or mechanically by oscillation,
    exposing the array of mirrors and attached probes to a sample substance potentially containing molecular structures responsive to respective ones of the probes for attachment of respective molecular structures to respective ones of the probes,
    determining whether any of the mirrors after exposure to the sample substance have an optical or mechanical action that is different from their optical or mechanical action before such exposure for thereby determining whether any molecular structures have become attached to any of the probes, and
    identifying the mirror or mirrors having such optically or mechanically different action.

7. A method for testing a sample substance for the presence of target biologic molecules and pathogens sought to be detected comprising the steps of
    utilizing the micromirrors in an array of microelectromechanical mirrors in a digital micromirror device for forming an array of micromirror test sites at multiple locations,
    attaching molecular probes of known binding characteristics to the surfaces of each micromirror test site with the probes in each test site differing from the probes in other test sites in a known predetermined manner, such that the test site locations of the probes and their binding characteristics are known,
    applying to the array of micromirror test sites a sample substance containing molecules or pathogens responsive to respective ones of the probes for attachment of respective molecules or pathogens to respective ones of the probes,
    activating the array of micromirrors, and
    detecting changes, if any, in the activation of any of the micromirrors occurring as a result of the binding of target molecules or pathogens to probes in respective test sites, whereby the presence of a multiplicity of different target molecules and pathogens in the sample substance can be detected.

8. A method as set forth in claim 7 including the steps of attaching bioluminescent or chemiluminescent probes to the array of test sites and, after applying the sample substance to the array of mirrors, directing a light source onto the array of mirrors, projecting the resulting image onto a surface, determining the locations within the image that fluoresce, and identifying the mirror or mirrors that correspond to the fluorescent locations.

9. A method as set forth in claim 7 including the steps of oscillating the mirrors in the array, applying the sample substance to the oscillating mirrors and detecting and identifying by software interrogation the mirrors whose rate of oscillation changes.

10. A method as set forth in claim 7 including the steps of isolating the mirror or mirrors in which a change was detected, removing therefrom the respective probe and any associated substance, and testing the same for the presence and identification of molecular structures sought to be detected.

* * * * *